US009717584B2

(12) United States Patent
Cully et al.

(10) Patent No.: US 9,717,584 B2
(45) Date of Patent: Aug. 1, 2017

(54) MEDICAL APPARATUS AND METHOD OF MAKING THE SAME

(75) Inventors: Edward H. Cully, Flagstaff, AZ (US); Edward E. Shaw, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 11/735,330

(22) Filed: Apr. 13, 2007

(65) Prior Publication Data

US 2008/0255594 A1 Oct. 16, 2008

(51) Int. Cl.
*A61F 2/04* (2013.01)
*A61F 5/00* (2006.01)
(Continued)

(52) U.S. Cl.
CPC .............. *A61F 2/04* (2013.01); *A61F 5/0003* (2013.01); *A61F 2002/044* (2013.01); *A61F 2002/061* (2013.01); *A61F 2002/8486* (2013.01); *A61F 2250/0023* (2013.01); *A61F 2250/0024* (2013.01); *A61F 2250/0071* (2013.01)

(58) Field of Classification Search
CPC .. A61F 2/04; A61F 5/0003; A61F 2250/0024; A61F 2250/0071; A61F 2002/061; A61F 2002/044; A61F 2002/8486; A61F 5/0013; A61F 5/0076;
(Continued)

(56) References Cited

U.S. PATENT DOCUMENTS 3,168,092 A   2/1965   Silverman
4,077,610 A   3/1978   Masuda
(Continued)

FOREIGN PATENT DOCUMENTS

EP   0 103 481   3/1984
EP   0 584 352   3/1997
(Continued)

OTHER PUBLICATIONS

Milone L, Gagner M, Ueda K, et. al. Effect of a Polyethylene Endoluminal Duodeno-Jejunal Tube (EDJT) on Weight Gain: A Feasibility Study in a Porcine Model. Obesity Surgery May 2006; v16 n5 : 620-626.
(Continued)

*Primary Examiner* — Corrine McDermott
*Assistant Examiner* — Tin Nguyen
(74) *Attorney, Agent, or Firm* — Amy L. Miller

(57) ABSTRACT

The invention relates to a novel medical apparatus for treatment of obesity, diabetes, and/or other obesity-associated health problems. The apparatus is used to impede absorption of nutrients within the gastrointestinal tract, i.e., substantially isolating nutrients from a portion of the gastrointestinal tract. The apparatus can be implanted using minimally invasive techniques, such a transesophageal approach under visualization. More specifically, the apparatus is used to impede absorption of nutrients within the gastrointestinal tract, i.e., substantially isolating nutrients from a portion of the gastrointestinal tract. The apparatus may include a sleeve and at least one anchoring component attached to the sleeve with a releasable component. The sleeve may have different properties along its length or there may be multiple sleeves having different properties.

18 Claims, 6 Drawing Sheets

(51) Int. Cl.
*A61F 2/06* (2013.01)
*A61F 2/848* (2013.01)

(58) Field of Classification Search
CPC ............ A61F 5/0079; A61F 2002/045; A61M 2025/0057
USPC ....... 606/157, 191, 151, 153, 154; 623/1.13, 623/1.15, 1.16, 23.7, 23.65, 23.64, 1.11, 623/23.75, 1.35, 1.34, 1.2
See application file for complete search history.

(56) References Cited

U.S. PATENT DOCUMENTS

| | | | |
|---|---|---|---|
| 4,109,659 A | 8/1978 | Sheridan | |
| 4,133,315 A | 1/1979 | Berman et al. | |
| 4,134,405 A | 1/1979 | Smit | |
| 4,246,893 A | 1/1981 | Berson | |
| 4,254,774 A | 3/1981 | Boretos | |
| 4,271,839 A | 6/1981 | Fogarty et al. | |
| 4,315,509 A | 2/1982 | Smit | |
| 4,416,267 A | 11/1983 | Garren et al. | |
| 4,479,497 A | 10/1984 | Fogarty et al. | |
| 4,485,805 A | 12/1984 | Foster, Jr. | |
| 4,493,711 A | 1/1985 | Chin et al. | |
| 4,501,264 A | 2/1985 | Rockey | |
| 4,558,699 A | 12/1985 | Bashour | |
| 4,607,618 A | 8/1986 | Angelchik | |
| 4,641,653 A | 2/1987 | Rockey | |
| 4,694,827 A | 9/1987 | Weiner et al. | |
| 4,716,900 A | 1/1988 | Ravo et al. | |
| 4,723,547 A | 2/1988 | Kullas et al. | |
| 4,739,758 A | 4/1988 | Lai et al. | |
| 4,763,653 A | 8/1988 | Rockey | |
| 4,803,985 A | 2/1989 | Hill | |
| 4,863,440 A | 9/1989 | Chin | |
| 4,878,905 A | 11/1989 | Blass | |
| 4,886,062 A | 12/1989 | Wiktor | |
| 4,899,747 A | 2/1990 | Garren et al. | |
| 5,067,957 A | 11/1991 | Jervis | |
| 5,129,915 A | 7/1992 | Cantenys | |
| 5,171,305 A | 12/1992 | Schickling et al. | |
| 5,190,546 A | 3/1993 | Jervis | |
| 5,202,352 A | 4/1993 | Okada et al. | |
| 5,246,456 A | 9/1993 | Wilkinson | |
| 5,306,300 A | 4/1994 | Berry | |
| 5,603,950 A | 2/1997 | Ratjen et al. | |
| 5,628,786 A | 5/1997 | Banas et al. | |
| 5,662,713 A | 9/1997 | Andersen et al. | |
| 5,769,884 A * | 6/1998 | Solovay ................ | A61F 2/07 606/194 |
| 5,800,522 A | 9/1998 | Campbell et al. | |
| 5,817,015 A | 10/1998 | Adair | |
| 5,820,584 A | 10/1998 | Crabb | |
| 5,868,141 A | 2/1999 | Ellias | |
| 5,891,084 A | 4/1999 | Lee | |
| 5,925,683 A | 7/1999 | Park | |
| 6,039,721 A | 3/2000 | Johnson et al. | |
| 6,264,700 B1 | 7/2001 | Kilcoyne et al. | |
| 6,306,141 B1 | 10/2001 | Jervis | |
| 6,352,561 B1 | 3/2002 | Leopold et al. | |
| 6,355,056 B1 | 3/2002 | Pinheiro | |
| 6,395,019 B2 | 5/2002 | Chobotov | |
| 6,454,785 B2 | 9/2002 | De Hoyos Garza | |
| 6,530,951 B1 | 3/2003 | Bates et al. | |
| 6,551,350 B1 | 4/2003 | Thornton et al. | |
| 6,613,083 B2 | 9/2003 | Alt | |
| 6,645,242 B1 | 11/2003 | Quinn | |
| 6,656,219 B1 | 12/2003 | Wiktor | |
| 6,675,809 B2 | 1/2004 | Stack et al. | |
| 6,676,674 B1 | 1/2004 | Dudai | |
| 6,676,692 B2 | 1/2004 | Rabkin et al. | |
| 6,676,971 B2 | 1/2004 | Goupil et al. | |
| 6,677,318 B1 | 1/2004 | Beisel | |
| 6,699,276 B2 | 3/2004 | Sogard et al. | |
| 6,733,512 B2 | 5/2004 | McGhan | |
| 6,740,121 B2 | 5/2004 | Geitz | |
| 6,746,460 B2 | 6/2004 | Gannoe et al. | |
| 6,748,653 B2 | 6/2004 | Lindemans et al. | |
| 6,755,869 B2 | 6/2004 | Geitz | |
| 6,821,291 B2 | 11/2004 | Bolea et al. | |
| 6,869,438 B2 | 3/2005 | Chao | |
| 6,923,828 B1 | 8/2005 | Wiktor | |
| 6,946,002 B2 | 9/2005 | Geitz | |
| 7,025,791 B2 | 4/2006 | Levine et al. | |
| 7,037,344 B2 | 5/2006 | Kagan et al. | |
| 7,090,699 B2 | 8/2006 | Geitz | |
| 7,111,627 B2 | 9/2006 | Stack et al. | |
| 7,122,058 B2 | 10/2006 | Levine et al. | |
| 7,128,748 B2 | 10/2006 | Mooradian et al. | |
| 2001/0044595 A1 | 11/2001 | Reydel et al. | |
| 2002/0091395 A1* | 7/2002 | Gabbay ................ | A61F 5/0079 606/151 |
| 2002/0143387 A1 | 10/2002 | Soetikno et al. | |
| 2003/0040804 A1 | 2/2003 | Stack et al. | |
| 2003/0040808 A1 | 2/2003 | Stack et al. | |
| 2003/0109931 A1 | 6/2003 | Geitz | |
| 2003/0191476 A1 | 10/2003 | Smit | |
| 2003/0199805 A1* | 10/2003 | McWeeney ...................... | 604/8 |
| 2003/0199989 A1 | 10/2003 | Stack et al. | |
| 2003/0199990 A1 | 10/2003 | Stack et al. | |
| 2004/0034407 A1* | 2/2004 | Sherry ......................... | 623/1.15 |
| 2004/0039452 A1 | 2/2004 | Bessler | |
| 2004/0044354 A1 | 3/2004 | Gannoe et al. | |
| 2004/0092892 A1 | 5/2004 | Kagan et al. | |
| 2004/0092974 A1 | 5/2004 | Gannoe et al. | |
| 2004/0107004 A1 | 6/2004 | Levine et al. | |
| 2004/0116848 A1 | 6/2004 | Gardeski et al. | |
| 2004/0122503 A1* | 6/2004 | Campbell et al. ........... | 623/1.12 |
| 2004/0133147 A1 | 7/2004 | Woo | |
| 2004/0148034 A1 | 7/2004 | Kagan et al. | |
| 2004/0172142 A1 | 9/2004 | Stack et al. | |
| 2004/0172143 A1 | 9/2004 | Geitz | |
| 2004/0204768 A1 | 10/2004 | Geitz | |
| 2004/0219186 A1 | 11/2004 | Ayres | |
| 2004/0220682 A1 | 11/2004 | Levine et al. | |
| 2004/0249362 A1 | 12/2004 | Levine et al. | |
| 2005/0043817 A1 | 2/2005 | McKenna et al. | |
| 2005/0049718 A1* | 3/2005 | Dann ......................... | A61F 2/04 623/23.65 |
| 2005/0075622 A1 | 4/2005 | Levine et al. | |
| 2005/0080395 A1 | 4/2005 | Levine et al. | |
| 2005/0080431 A1 | 4/2005 | Levine et al. | |
| 2005/0080491 A1 | 4/2005 | Levine et al. | |
| 2005/0085787 A1 | 4/2005 | Laufer | |
| 2005/0085923 A1* | 4/2005 | Levine et al. ............. | 623/23.65 |
| 2005/0096750 A1 | 5/2005 | Kagan et al. | |
| 2005/0125020 A1* | 6/2005 | Meade et al. ................. | 606/191 |
| 2005/0125075 A1 | 6/2005 | Meade et al. | |
| 2005/0131515 A1 | 6/2005 | Cully et al. | |
| 2005/0137677 A1* | 6/2005 | Rush ........................... | 623/1.13 |
| 2005/0154448 A1 | 7/2005 | Cully et al. | |
| 2005/0177181 A1* | 8/2005 | Kagan ............... | A61B 17/00234 606/151 |
| 2005/0192615 A1 | 9/2005 | Torre et al. | |
| 2005/0197714 A1* | 9/2005 | Sayet ......................... | 623/23.65 |
| 2005/0228480 A1* | 10/2005 | Douglas et al. ............. | 623/1.13 |
| 2005/0240279 A1 | 10/2005 | Kagan et al. | |
| 2005/0256587 A1 | 11/2005 | Egan | |
| 2005/0273060 A1 | 12/2005 | Levy et al. | |
| 2006/0009858 A1 | 1/2006 | Levine et al. | |
| 2006/0015125 A1 | 1/2006 | Swain | |
| 2006/0015167 A1* | 1/2006 | Armstrong et al. ........... | 623/1.2 |
| 2006/0015175 A1* | 1/2006 | Armstrong .................... | 623/1.12 |
| 2006/0020254 A1 | 1/2006 | Hoffmann | |
| 2006/0025851 A1* | 2/2006 | Khan et al. .................. | 623/1.16 |
| 2006/0025852 A1 | 2/2006 | Armstrong et al. | |
| 2006/0030949 A1* | 2/2006 | Geitz ......................... | 623/23.65 |
| 2006/0058829 A1 | 3/2006 | Sampson | |
| 2006/0064120 A1 | 3/2006 | Levine et al. | |
| 2006/0122691 A1 | 6/2006 | Richter | |
| 2006/0155312 A1 | 7/2006 | Levine et al. | |
| 2006/0161139 A1 | 7/2006 | Levine et al. | |
| 2006/0161172 A1 | 7/2006 | Levine et al. | |
| 2006/0161187 A1 | 7/2006 | Levine et al. | |

(56) References Cited

U.S. PATENT DOCUMENTS

| | | |
|---|---|---|
| 2006/0161241 A1 | 7/2006 | Barbut et al. |
| 2006/0161265 A1 | 7/2006 | Levine et al. |
| 2006/0212042 A1 | 9/2006 | Lamport et al. |
| 2007/0005147 A1 | 1/2007 | Levine et al. |
| 2007/0027548 A1 | 2/2007 | Levine et al. |
| 2007/0083271 A1 | 4/2007 | Levine et al. |
| 2007/0142896 A1 | 6/2007 | Anderson |
| 2007/0156248 A1* | 7/2007 | Marco ................ A61F 2/02 623/23.7 |
| 2008/0015674 A1 | 1/2008 | Austin et al. |

FOREIGN PATENT DOCUMENTS

| | | |
|---|---|---|
| EP | 0 815 806 | 6/1997 |
| EP | 0 819 412 | 1/1998 |
| EP | 1 700 580 | 9/2008 |
| FR | 2 862 525 | 5/2005 |
| JP | 2000-503874 A | 4/2000 |
| JP | 2005-516670 A | 6/2005 |
| JP | 2006507910 | 3/2006 |
| WO | 90/01879 | 3/1990 |
| WO | 98/27894 | 7/1998 |
| WO | 2004/041133 | 5/2004 |
| WO | WO2005/060869 | 7/2005 |
| WO | 2005/082296 | 9/2005 |
| WO | 2005/110280 | 11/2005 |
| WO | 2006/028925 | 3/2006 |
| WO | 2007136468 | 11/2007 |
| WO | 2008030403 | 3/2008 |
| WO | WO2008/127552 | 10/2008 |

OTHER PUBLICATIONS

Povoas, H Staplerless Laparoscopic Gastric Bypass: Not So Fast. Obesity Surgery Aug. 2006; v16 n8:1115-1116.

Satiety, Inc.'s New Transoral Procedure for Treating Obesity Shows Promising Results in First Clinical Trial. http://www.allbusiness.com/services/business-services/3939777-1.html Oct. 26, 2006.

Jun. 2, 2009; International Search Report and Written Opinion, International application No. PCT/US2009/002229.

Extended European Search Report dated Mar. 15, 2016 for EP 15 19 3823.

* cited by examiner

MEDICAL APPARATUS AND METHOD OF MAKING THE SAME

BACKGROUND OF THE INVENTION

Field of the Invention

The invention relates to a medical apparatus including a device used in the treatment of obesity and potentially other associated health problems, e.g., type II diabetes. More specifically, the apparatus is used to impede absorption of nutrients within the gastrointestinal tract, i.e., substantially isolating nutrients from a portion of the gastrointestinal tract.

Discussion of the Related Art

Currently, obesity and related health problems are on the rise in the United States and in other industrialized countries. For example, the latest data from the National Center for Health Statistics show that 30 percent of U.S. adults 20 years of age and older—over 60 million people—are obese. Unfortunately, the increase in obesity rates is not limited to adults and the percentage of young people who are overweight has more than tripled since 1980. For example, among children and teens aged 6-19 years, 16 percent (over 9 million young people) are considered overweight.

Obesity may lead to a number of health problems including, for example, hypertension, dyslipidemia (e.g., high total cholesterol or high levels of triglycerides), diabetes (e.g., Type 2 diabetes), coronary heart disease, stroke, gallbladder disease, osteoarthritis, sleep apnea and respiratory problems, cancers (e.g., endometrial and breast), and other ill-health effects. See e.g., Kanders, B. S., et al., Weight loss outcome and health benefits associated with the Optifast program in the treatment of obesity. Int J Obes, 1989. 13: p. 131-134.

Currently, there are a number of devices and methods for treating obesity, including such surgical procedures as biliopancreatic diversion, silastic ring gastroplasty, jejunoileal bypass, gastric bypass, Roux-en-Y gastric bypass, gastroplasty, gastric banding, vertical banded gastroplasty, and staged procedures. Unfortunately, these procedures have a number of drawbacks including the possibility of severe complications associated with invasive and complicated procedures such as organ failure and even death.

Other less severe complications may include dumping syndrome. Dumping syndrome occurs when the contents of the stomach empty too quickly into the small intestine. The partially digested food draws excess fluid into the small intestine causing nausea, cramping, diarrhea, sweating, faintness, and/or palpitations. Dumping syndrome usually occurs after the consumption of too much simple or refined sugar by people who have had surgery to modify or remove part of the stomach.

SUMMARY OF THE INVENTION

The present invention is directed to an apparatus and method of making the same.

An advantage of the invention is to provide an apparatus having a sleeve that has at least two regions of different properties, e.g., porosity, thickness, pore size and the like.

Another advantage of the present invention is to provide a sleeve that is releasable from an anchoring component via a releasable component.

Still another advantage of the invention is to provide a sleeve that is releasable from itself with a releasable component.

Additional features and advantages of the invention will be set forth in the description or may be learned by practice of the invention. These features and other advantages of the invention will be realized and attained by the structure particularly pointed out in the written description and claims hereof as well as the appended drawings.

To achieve these and other advantages and in accordance with the purpose of the invention, as embodied and broadly described, an apparatus for placement in a portion of the gastrointestinal tract includes a sleeve and at least one anchoring component attached to the sleeve with a releasable component.

In another aspect of the invention, the apparatus for placement in a gastrointestinal tract includes at least one anchoring component and a sleeve attached to at least one anchoring component. The sleeve includes at least a first region and a second region attached to each other with a releasable component. The first and second regions may have different properties, e.g., porosities, pore size, thickness, and the like. In addition, the properties may change in-situ after a predetermined time.

In another aspect of the invention, the apparatus includes a sleeve having a proximal end, a distal end, an inner surface, an outer surface, and a wall thickness. The sleeve also includes at least one portion that is detachable from the remainder of the tube. The anchoring component is attached to a proximal end of the tube with a releasable component.

In another aspect of the present invention, the apparatus includes a sleeve having a proximal end, a distal end, an inner surface, an outer surface, and a wall thickness. An anchoring component is attached to the proximal end of the sleeve with a releasable component, such that the sleeve decouples from the anchoring component when the releasable component weakens after a predetermined time.

In another aspect of the invention, the apparatus includes a first anchoring component sized to be located in a patient's duodenum. A first sleeve is attached to and extends from the first anchoring component. The first sleeve has a proximal end, a distal end, an inner surface, an outer surface, a wall portion extending from the proximal end to the distal end, and at least one opening in the wall portion. The apparatus also includes a second anchoring component sized to be located in the patient's biliary duct and a second sleeve attached to and extending from the second anchoring component. The second sleeve is sized to fit through at least one opening in the wall portion of the first sleeve.

It is to be understood that both the foregoing general description and the following detailed description are exemplary and explanatory and are intended to provide further explanation of the invention as claimed.

BRIEF DESCRIPTION OF THE DRAWINGS

The accompanying drawings are included to provide a further understanding of the invention and are incorporated in and constitute a part of this specification, illustrate embodiments of the invention, and together with the description serve to explain the principles of the invention.

In the drawings.

DETAILED DESCRIPTION OF THE ILLUSTRATED EMBODIMENTS

Figure 1A:
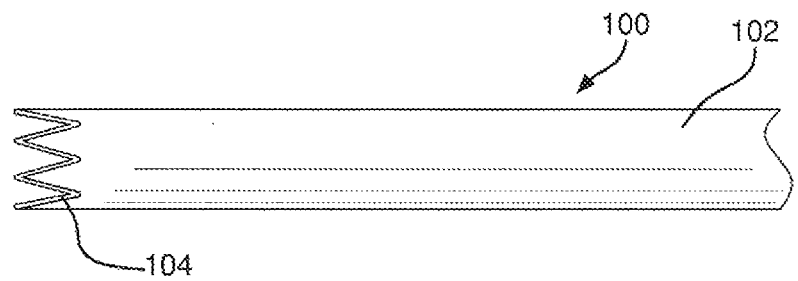
FIG. 1A illustrates an apparatus according to an embodiment of the invention.

The invention relates to a novel medical apparatus for treatment of obesity, diabetes, weight loss and/or other obesity-associated health problems. The apparatus is used to impede absorption of nutrients within the gastrointestinal tract, i.e., substantially isolating nutrients from a portion of the gastrointestinal tract. The apparatus can be implanted using minimally invasive techniques, such a transesophageal approach under visualization and others as known in the art.

In one embodiment, the apparatus includes a sleeve and at least one anchoring component. The anchoring component is attached to at least a portion of the sleeve with a releasable component or a coupling agent as known in the art. The coupling agent may include a starch, cyanoacrylates, silicone, urethane, and/or thermoplastics, e.g., nylon, perfluoroalkoxy (PFA), polyurethane (PU), fluorinated ethylene propylene (FEP), and others as known in the art. Preferably, the coupling agent has acceptable biocompatibility and is formed from copolymers, such as a tetrafluoroethylene perfluoroalkylvinylether copolymer (TFE/PAVE), a tetrafluoroethylene perfluoromethylvinylether copolymer (TFE/PMVE), and combinations thereof. Of course, bioabsorable materials may also be used such as polyglycolic acid and trimethylene carbonate monomer (PGA/TMC), polyglycolic acid and polylactic acid (PGA/PLA), and combinations thereof.

The anchoring component is optional and the sleeve may be attached to a patient via other attachment mechanisms. For example, the sleeve may be directly attached to a patient's anatomy by a variety of attachment mechanisms as known in the art, e.g., sutures, staples, adhesives, anchors, hooks, or combinations thereof and the like.

The anchoring component may be attached to an inner or outer surface of the sleeve. The releasable component may be an active, passive component, and combinations of the same. An active releasable component is one that requires some outside intervention to facilitate its release. For example, a pull mechanism, such as string, tab, and the like other mechanisms may include an external source, such as an energy source, chemical source, thermal source, combinations thereof and the like. Energy sources may include ultrasonic energy, electromechanical energy, magnetic energy and the like. Chemical sources may include different solutions, e.g., a solution at least temporarily changing the pH of the gastrointestinal tract or others. A passive releasable component is one that releases over time without any outside intervention. For example, a passive releasable component may include a degradable material that has a predetermined decay cycle in the given anatomy. In some embodiments, the degradable material includes a bioabsorbable material, biodigestible material, and/or combinations thereof discussed herein.

The sleeve is a conduit for transporting ingested materials, e.g., pre-digested food, chyme, gastrointestinal material and fluids found in the stomach, and the like. The sleeve is designed to permit at least partial isolation of ingested and/or gastrointestinal fluids, such as, bile and pancreatic juices, from at least portions of the gastrointestinal tract. For example, the sleeve may permit at least partial isolation of chyme from at least portions of villi in the gastrointestinal tract. Preferably, the sleeve is at least a partially compressible conduit that does not substantially inhibit peristaltic mechanisms of the gastrointestinal tract and/or other mechanisms of transport, thereby permitting transport of ingested materials throughout the conduit.

The sleeve may include a plurality of different materials attached together with a releasable component. More specifically, the sleeve may include a first region and a second region attached to each other with a releasable component. Again, the releasable component may be either a passive or active releasable component as previously described. In a preferred embodiment, the release component includes sutures.

The sleeve may include a plurality of different materials, thereby forming regions of different properties, e.g., porosity, pore size, thickness, and the like. Porosity is expressed in percent porosity and may be determined by calculating the quotient of the density of the article and that of the bulk density of PTFE and multiplying that quotient by 100%. For the purposes of this calculation, the bulk density of PTFE was taken to be 2.2 g/cc.

When it is desired to completely isolate ingested materials from the gastrointestinal tract the preferred porosity is about 0%. When it is desired to change the degree of isolation over time it is preferred to fill the pores of the sleeve with a degradable material, e.g., bioabsorable material that will be absorbed over a predetermined time. In this case, the starting sleeve may be porous, that is possessing a pore size large enough to pass nutrients and/or gastrointestinal fluids through the sleeve wall. For example, the porosity of sleeve may be in the range of about 0% to about 85% or more.

Pore size can be estimated to be an average of the largest dimension of the pore. In porous expanded ePTFE materials pore size may be estimated by an average length of the fibrils. Fibril lengths on the order of 20 microns may allow the passage of nutrients to the gastrointestinal tract. Pore size of the sleeve may be in the range from about 0 microns to 6 mm or more. The pore size may be substantially uniform or non-uniform and may vary throughout the sleeve. For example, the sleeve may be rendered macro-porous to have 6 mm holes throughout at least a portion of the sleeve. The rendering may be conducted by any known means in the art, for example, the sleeve may be hole punched, laser treated, etched, combinations thereof and the like. The pore size may be designed to allow preferential passage of targeted nutrients and/or gastrointestinal fluids through the sleeve wall or a portion of the sleeve wall.

The properties of the different regions of the sleeve may degrade over time or be fixed throughout the implant life of the life sleeve. For example, when utilizing a bioabsorable material over a portion of the porous sleeve, as the bioabsorable material degrades, the porosity of the sleeve will change. In one embodiment, various sleeve segments having different porosity may be attached together with a releasable component. More specifically, the sleeve may include a first region and a second region attached to each other with a releasable component. Again, the releasable component may be either a passive or active releasable component as previously described. In a preferred embodiment, the release component includes sutures.

In another embodiment, the sleeve was constructed to have a releasable component attaching at least a portion of the sleeve together. For example, the sleeve may be formed with a longitudinal seam being attached together with a releasable component.

In another embodiment, the apparatus includes a first anchoring component sized to be located in a patient's duodenum and a first sleeve attached to and extending from the first anchoring component. The first sleeve has a proximal end, a distal end, an inner surface, an outer surface, a wall portion extending from the proximal end to the distal end, and at least one opening in the wall portion. A second anchoring component is sized to be located in the patient's biliary duct. The second sleeve is attached to and extending from the second anchoring component.

The sleeve may also include markings to allow a physician to determine the appropriate deployment, e.g., orientation, location, etc., of the sleeve or alternatively to allow tailoring the sleeve to the desired length. The markings may also include a radiopaque material to aid in non-invasive visualization or other suitable visualization materials as known in the art. For example, the sleeve may have at least one longitudinal strip of radiopaque material incorporated into at least a portion of the length of the sleeve.

A physician may tailor the sleeve into any length suitable for treatment of obesity and/or diabetes as determined necessary. For example, the sleeve may have a length ranging from about 2 cm to 1000 cm. Preferably, the length of the sleeve ranges from about 50 cm to 200 cm.

The sleeve may be designed to have any number of different geometrically shaped cross-sections, such as circular, oval, elliptical, diamond, square, combinations thereof and the like. In addition, the sleeve may narrow along its length, e.g., having a tapered shape. More specifically, a cross-section at one end of sleeve may be larger than a cross-section at an opposite end of the sleeve. Preferably, the sleeve is designed to have a circular cross-section. In addition, the sleeve may include localized regions of restricted or enlarged cross-sections.

The outside dimension of the sleeve is preferably sized to permit the sleeve to fit within a patient's internal gastrointestinal tract. The outside dimension of the sleeve may also be oversized or undersized within a patient's gastrointestinal tract, that is, the outermost dimension, e.g., the outside diameter may be greater or less than the diameter of the gastrointestinal tract. Preferably, when utilizing a sleeve with a circular cross-section the outside diameter may be in the range from about 15 mm to about 50 mm, and more preferably, the outside diameter ranges from about 20 mm to 30 mm.

The sleeve is preferably sized and designed to be suitably flexible enough to permit peristaltic mechanisms of the gastrointestinal tract and/or other mechanisms of transport down the length of the sleeve. The thickness is chosen to permit transport of ingested materials throughout the conduit via peristaltic or other mechanisms. Preferably, the thickness of the sleeve ranges from about 0.003 mm to about 2.6 mm, and more preferably, it ranges from about 0.02 mm to about 0.7 mm thick. The thickness of the sleeve may also vary along the length of the sleeve, for example, the sleeve may be thicker at one end and thinner at an opposite end.

Multiple manufacturing techniques may be used to form the sleeve as known in the art. For example, these techniques can take the form of an extruded or otherwise formed sleeve of a composition that provides mechanical and physical properties that allow at least partial isolation of material exiting the stomach from the small intestine. For example, the sleeve provides at least partial isolation of ingested materials within the sleeve from the digestive tract environment. This isolation may be complete, incomplete, and may vary over time the sleeve is in the patient, vary down the length of the sleeve, and combinations of the same. Preferably, the isolation is designed to provide at least partially impaired absorption of nutrients down a portion of the small intestine, thereby promoting weight loss in the patient.

The sleeve can be constructed, in whole or in part, utilizing a variety of degradable materials, polymeric materials, synthetic or natural, and combinations thereof. In some embodiments, the sleeve may be composed of multiple components that are mixed as a blend, such as a plasticized system, and/or as a microphase immiscible system. If suitable reactive groups are introduced into the formed sleeve, what is commonly known as a thermoset or chemically cross-linked system can be generated under appropriate curing conditions. The formed sleeve can also be composed in the form of a laminate or a fibrous reinforced composite. Of course, the properties of the selected composition, e.g., molecular weight, glass transition temperature(s), crystallinity, and/or the extent of cross-linking will dictate the desired properties of the sleeve. The sleeve may also be coated with a variety of therapeutic agents such as vitamin coatings, drug coatings, and the like. The vitamin coatings may be designed to mimic or supplement therapeutic vitamin therapies implemented to patients of traditional weight loss therapies.

In a preferred embodiment, the sleeve is constructed from a composite of ePTFE and FEP materials. The composite has FEP layer on one side of the laminate and ePTFE on the opposite side. The composite film possesses the following properties: a thickness ranging from about 0.002 mm to about 0.7 mm, and more preferably, it ranges from about 0.02 mm to about 0.3 mm thick. An EPA bubble point of greater than about 0.6 MPa, and a tensile strength of at least about 75 MPa in the weakest direction. More preferably, also having a tensile strength of about 309 MPa in the strongest direction. In a preferred embodiment, the resultant sleeve is impermeable to gastrointestinal fluids, e.g., chyme, biliopancreatic fluids, digested foods, stomach acids and the like.

The sleeve may be fabricated in a continuous or batch process as known in the art. In one embodiment, a plurality of film strips may be arranged in the longitudinal direction along the length of a mandrel. The strips may be evenly or non-evenly spaced along the length of mandrel, that is, the strips may overlap or not overlap with each other. In a preferred embodiment, the strips are a composite film of FEP and ePTFE, however, other sleeve materials as described herein may be utilized. In this embodiment, an adhesive FEP side of the film may be arranged such that it is up or away from the mandrel.

The mandrel with the longitudinal oriented film may then be helically wrapped with another composite film. The helically wrapped film may be the same or different type material as the previously used composite film. The FEP adhesive may be oriented down towards the mandrel and against the longitudinal film. A helical wrapper may be used to apply the film at a predetermined pitch. Pitch is defined as the amount of advance per revolution of the mandrel. The longitudinal and helical wrapping processes may be repeated one or more times.

The film layered mandrel may then be placed into an oven, e.g., air convection oven set to a temperature ranging from about 250 to 400° C., and more preferably to a temperature ranging from about 300 to 340° C. It may be heated in the oven for time ranging from about 15 to 60 minutes, and more preferably for a time ranging from about 25 to 35 minutes. Upon removal from the oven the resultant sleeve is cooled to room temperature. Alternatively, other suitable techniques as known in the art may be utilized in fabrication of the sleeve.

The anchoring component may be a self-expandable, balloon-expandable or a combination of self-expandable and balloon-expandable anchoring components. In some embodiments, the anchoring component is used to at least partially fix the device inside a portion of the gastrointestinal tract, e.g., before, across, or after the pylorus. Other anchoring locations are also possible, for example it may be arranged in the esophagus; at the gastroesophageal interface; in the stomach such as prior to the pylorus, e.g., in the stomach antrum; across the pylorus; in the duodenum bulb; in the small intestine or at another suitable site.

The anchoring component is preferably constructed from materials that are flexible and strong. The anchoring component may be formed from degradable bioabsorable materials, biodigestible materials, polymeric materials, metallic materials and combinations thereof. In addition, these materials may be reinforced and/or coated with other materials, such as polymeric materials and the like. The coating may be chosen to reduce acidic or basic effects of the gastrointestinal tract, e.g., with a thermoplastic coating such as ePTFE and the like.

The anchoring component may be formed into a variety of different geometric configurations having constant and/or varied thickness as known in the art. The geometric configurations may include many conventional stent configurations such as a helical wrapped stent, z-shape stent, tapered stent, coil stent, combinations and the like. Moreover, the anchoring component may be designed to have a flange on one side and a coil shape on the opposite side. Preferably, the anchoring component has a tapered configuration, that is, where one end of the component has a larger dimension than the opposite end. This tapered configuration is thought to provide better anchoring proximally or distally to the pylorus.

The anchoring component may be designed to degrade or decompose over time. For example, the anchoring component may be designed to degrade with exposure to the acidic or basic environment of the anatomy. In these configurations, the anchoring component may be constructed from biodigestible materials and/or bioabsorable materials. Biodigestible materials include acidic or basic degradable metals and alloys, such as, iron, aluminum, chromalloy, and the like. Of course, other materials that degrade over time as known in the art may also be utilized in the fabrication of the anchoring component.

By way of example, bioabsorable self-expanding anchoring components may be manufactured as taught in U.S. Patent Application Publication 2006/0025852. For example, an integral framework in a substantially tubular shape can be utilized. The integral framework elements include bioabsorable materials such as these described herein. In one embodiment, the materials include non-blended hydrolysable polymer material in a tri-block co-polymer of poly(glycolide) and poly(trimethylenecarbonate).

In another embodiment, the anchoring component is constructed from a super-elastic material such as nitinol. The material may be formed from a cut tube material or wire material. The material is sized to have a thickness ranging from about 0.01 to 0.5 mm or more. The material may have any cross-sectional geometry, e.g., a circle, oval, square, triangle, ribbon and the like.

The anchoring component may be manufactured as known in the art, e.g., laser cutting a tube. In one embodiment, the anchoring component is formed from a wire, e.g., nitinol wire. The wire is arranged around variously spaced pins on a jig. The pins are spaced on the jig into a desired geometric pattern. The pins act to hold the wire in a desired shape during a subsequent thermal setting process. In addition, the jig may be tapered or straight along a longitudinal axis. Preferably, the jig is constructed from a stainless steel cylinder. The wire is wrapped around the various pins to form the anchoring component. Each end of the wire is terminated under a termination unit, e.g., screw head that hold an end of the wire.

The wire and jig are placed into a heat source, e.g., a convection oven, at a shape setting temperature. Preferably, when utilizing super-elastic nitinol wire the shape setting temperature ranges from about 440° C. to 500° C., and more preferably from about 460° C. to 480° C. The super-elastic nitinol wire is placed into the heat source for time ranging from about 10 to 40 minutes, and more preferably for time from about 15 to 20 minutes. Upon removal, the jig and wire are submersed in a water bath at room temperature. After the jig has cooled and dried the anchor component is removed and any excess wire may be trimmed.

Degradable materials include bioabsorable materials and biodigestible materials as discussed herein. Biodigestible includes a material that is capable of being converted into assimilable condition in the alimentary canal or capable of being at least partially decayed to allow passing of the material. Bioabsorable materials include bioabsorable polymers and copolymers composed from varying amounts of one or more of the following monomer examples, glycolide, d,l-lactide, l-lactide, d-lactide, p-dioxanone (1,4-dioxane-2-one), trimethylene carbonate (1,3-dioxane-2-one), ε-caprolactone, γ-butyrolactone, δ-valerolactone, 1,4-dioxepan-2-one, and 1,5-dioxepan-2-one. Polymers that are either introduced as or can be degraded to segment lengths that can be excreted from the body can also be considered as bioabsorable, and may include polyethylene glycol, polypropylene glycol, amino acids, anhydrides, orthoesters, phosphazines, amides, urethanes, and phosphoesters. Alternative copolymers may possess, in whole or in part, block, segmented, random, alternating, or statistical polymeric construction characteristics. Animal derived products such as elastin or collagen, either absorbable, e.g., enzymatically degraded, within the body or rendered non-absorbable through chemical treatment, e.g., glutaraldehyde cross-linked bovine pericardium, may alternatively be utilized as or within the sleeve construct. Additional potential components of the sleeve may include naturally derived or modified polysaccharides such as chitosan, alginate, and/or hyaluronic acid.

Reference will now be made in detail to embodiments of the invention, examples of which are illustrated in the accompanying drawings.

Figure 1B:
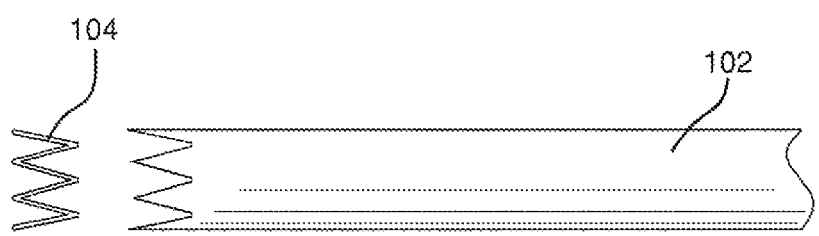
FIG. 1B illustrates the apparatus of FIG. 1A having component separation.
Figure 1C:
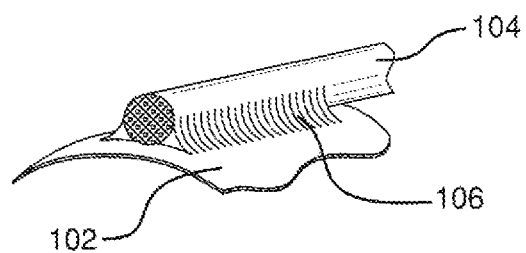
FIG. 1C illustrates a expanded view of a portion of FIG. 1A.

FIG. 1A illustrates a sleeve according to an embodiment of the invention. FIG. 1B illustrates a sleeve detached from an anchoring component according to FIG. 1A. FIG. 1C illustrates an expanded view of FIG. 1A.

Referring to FIGS. 1A-1C, an implantable apparatus is generally depicted as reference number 100. The apparatus 100 includes a sleeve 102 and an anchoring component 104. The anchoring component 104 is attached to the sleeve 102 with a releasable component 106.

The releasable component 106 may be active or passive. In this embodiment the releasable component 106 includes a material applied in a pattern to a portion of the anchoring component 104. For example, the adhesive may be applied as a narrow strip of material to join a portion of the anchoring component to the sleeve. Preferably, the pattern is utilized on both sides of the anchoring component 104 as shown in FIG. 1C. However, the releasable component 106 may be arranged in any geometric pattern such as a circle, square, diamond, ring, line, and the like. The thickness and type of pattern utilized may be a factor in its release time.

In this embodiment, the releasable component is selected from a material that may decay over time such as a degradable material including at least one of the bioabsorable materials and biodigestible materials as discussed herein. The material is preferably a bioabsorable material, such as PGA/PLA or other materials as known in the art. In practice, the bioabsorable material decays at a predetermined time such that the sleeve 102 is released from the anchoring component 104. The sleeve is then free to travel through the rest of the gastrointestinal tract. After the sleeve is released there is no longer isolation of the chyme from gastrointestinal juices over at least a partial length of the sleeve and gastrointestinal tract.

Figure 2A:
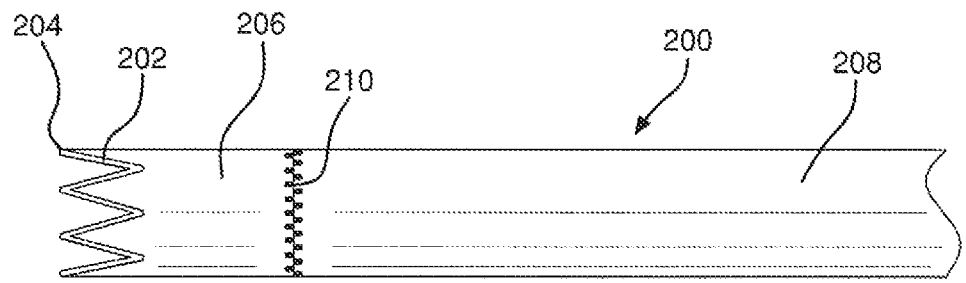
FIG. 2A illustrates an apparatus according to another embodiment of the invention.
Figure 2B:
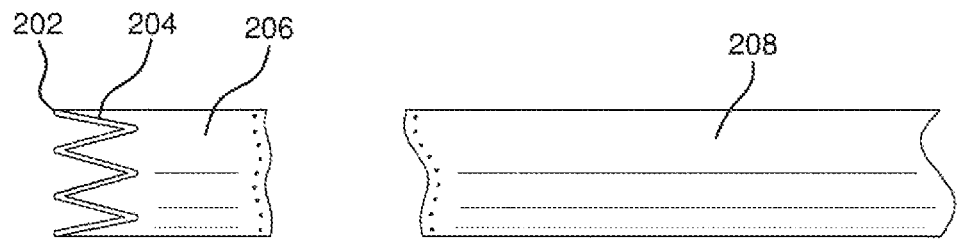
FIG. 2B illustrates the apparatus of FIG. 2A having component separation.
Figure 2C:
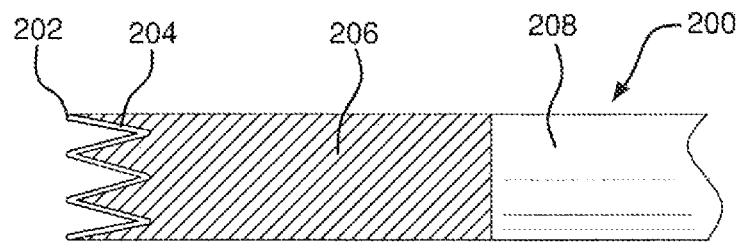
FIG. 2C illustrates an apparatus according to FIG. 2A having sections of different properties.

FIG. 2A illustrates an implantable apparatus according to another embodiment of the invention. FIG. 2B illustrates the implantable apparatus of FIG. 2A having component separation. FIG. 2C illustrates an implantable apparatus according to FIG. 2A having sections of different properties.

Referring to FIGS. 2A-2C an implantable apparatus is generally depicted as reference number 200. The apparatus 200 includes a sleeve and an anchoring component 202. The anchoring component 202 is attached to the sleeve with an adhesive 204 as known in the art. The adhesive 204 may be attached to any portion of the anchoring component 202 or a fully covered portion of the anchoring component 202. For example, the adhesive may be applied in a pattern, e.g., a narrow strip of material to join a portion of the anchoring component 202 to the sleeve. Preferably, the pattern is utilized on both sides of the anchoring component 202. Again, the adhesive 204 may be arranged in any geometric pattern such as a circle, ring, line, and the like. The thickness and type of pattern utilized may be a factor in its strength. Alternatively, the anchoring component may be attached to the sleeve with a releasable component as described herein, e.g., as shown in FIGS. 1A-1C.

The sleeve includes a first portion 206 and a second portion 208 arranged together with a releasable component 210. In this embodiment, the first 206 and second 208 portions of the sleeve are circumferentially attached with an active releasable component 210. The active releasable component 210 is a filament arranged in a pattern such as a chain stitch. Preferably, the filament is a fluoropolymer suture, e.g., ePTFE suture. The filament 210 includes a free portion (not shown) to facilitate grasping and application of tension, thereby releasing the stitch as known in the art. The first 206 and second 208 portions of the sleeve may be constructed from the same material. Alternatively, the first and second portions of the sleeve may be constructed from different materials. The different sleeve materials may have different properties, e.g., different porosity, thereby permitting different absorption rates through the sleeve as illustrated in FIG. 2C. Alternatively, the first and second portions may be permanently attached to each other, e.g., with an adhesive.

There could also be a plurality of sleeve portions attached together to permit in-situ length adjustability. For example, there may be six equal or non-equal sleeve segments arranged together each having a releasable component. This would allow a physician to release a portion of the sleeve thereby permitting in-situ length adjustment. Any combination of releasable components may be utilized, e.g., active and/or passive components as described herein.

In another embodiment, the sleeve portions are attached with a passive releasable component. The passive releasable components are designed to permit sequential release of the sleeve portions. For example, the most distal sleeve portion may be released first and its adjacent portion released next, and so on. This is designed to permit automatic staged adjustment of the length of the sleeve.

Figure 3A:
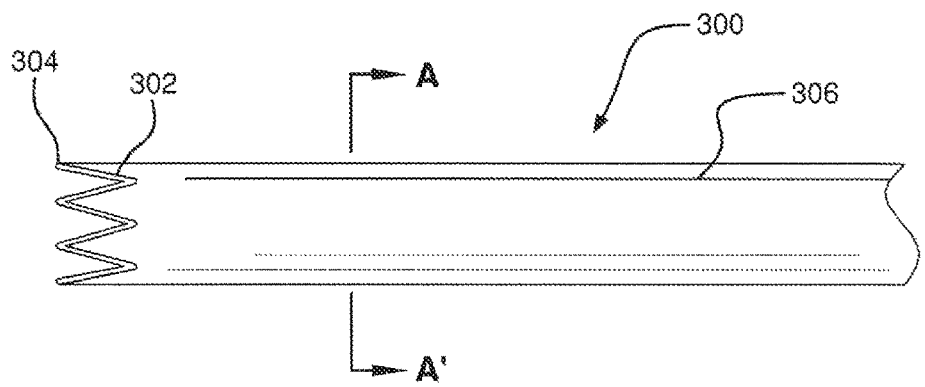
FIG. 3A illustrates an apparatus according to another embodiment of the invention.
Figures 3B, 3C:
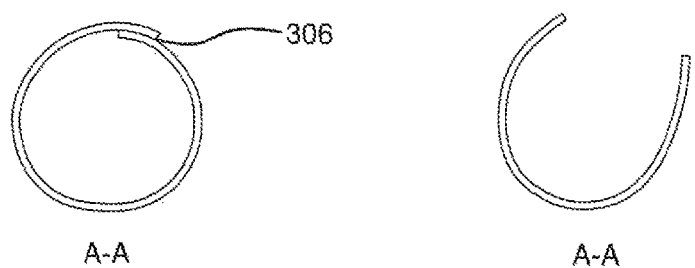
FIG. 3B illustrates a cross-sectional end view of the apparatus shown in FIG. 3A cut along line A to A' prior to release.
FIG. 3C illustrates a cross-sectional end view of the apparatus shown in FIG. 3A cut along line A to A' after release.

FIG. 3A illustrates an implantable apparatus according to another embodiment of the invention. FIG. 3B illustrates a cross-sectional end view of the apparatus shown in FIG. 3A cut along line A to A' prior to release. FIG. 3C illustrates a cross-sectional end view of the apparatus shown in FIG. 3A cut along line A to A' after release.

Referring to FIGS. 3A-3C an implantable apparatus is generally depicted as reference number 300. The anchoring component 302 is attached to the sleeve with an adhesive 304. The adhesive 304 may be attached to any portion of the anchoring component 302 as well as a fully covered portion of the anchoring component 302. For example, the adhesive 304 may be applied in a fillet pattern to a portion of the anchoring component 302. Preferably, the fillet pattern is utilized on both sides of the anchoring component 302. Again, the adhesive 304 may be arranged in any geometric pattern such as a circle, ring, line, and the like. The thickness and type of pattern utilized may be a factor in its strength. Alternatively, the anchoring component may be attached to the sleeve with a releasable component as described herein, e.g., as shown in FIGS. 1A-1C.

In this embodiment, the releasable component 306 is a passive releasable component, such as a degradable adhesive that may decay over time. The degradable material is preferably a bioabsorable adhesive material such as PGA/PLA or other materials as known in the art. FIG. 3C, illustrates a time after the adhesive 306 has decayed and the sleeve opens along the longitudinal seam. This embodiment permits automatic restoration of absorption of the villi in the gastrointestinal tract at a predetermined time, e.g., after 3 months or more.

Figure 4A:
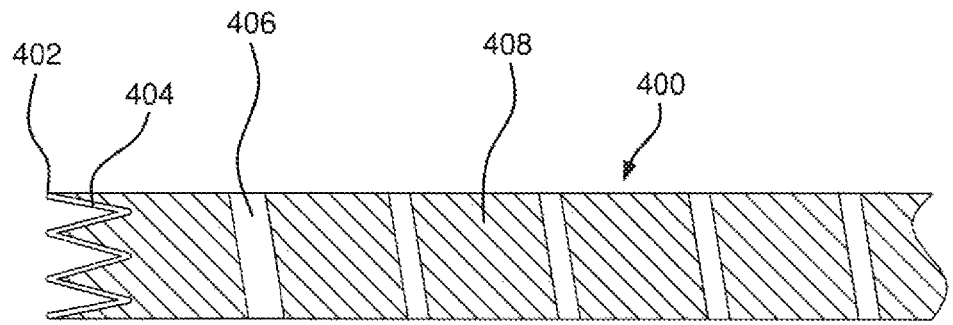
FIG. 4A illustrates an apparatus according to another embodiment of the invention.
Figure 4B:
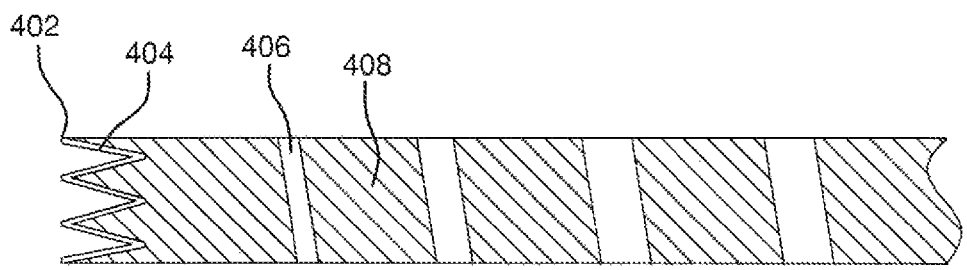
FIG. 4B illustrates an apparatus according to another embodiment of the invention.

FIG. 4A illustrates an implantable apparatus according to another embodiment of the invention. FIG. 4B illustrates an implantable apparatus according to another embodiment of the invention.

Referring to FIG. 4A an apparatus is generally depicted as reference number 400. The anchoring component 402 is attached to the sleeve with an adhesive 404. The adhesive 404 may be attached to any portion of the anchoring component 402 as well as a fully covered portion of the anchoring component 402. For example, the adhesive 404 may be applied in a fillet pattern to a portion of the anchoring component 402. Preferably, the fillet pattern is utilized on both sides of the anchoring component 402. Again, the adhesive 404 may be arranged in any geometric pattern such as a circle, ring, line, and the like. The thickness and type of pattern utilized may be a factor in its strength. Alternatively, the anchoring component may be attached to the sleeve with a releasable component as described herein, e.g., as shown in FIGS. 1A-1C.

In this embodiment, the sleeve includes areas of different porosities that change over time. For example, the sleeve includes a plurality of first porosity regions 406 and second porosity regions 408. The first set of porosity regions 406 permit nutrient absorption after a predetermined period of time. That is, these regions are designed to allow chyme and other gastrointestinal juices to reach the villi of the small intestine after a predetermined period of time.

The second set of porosity regions 408 substantially minimizes or prevents nutrient absorption, e.g., prevents or minimizes chyme and other gastrointestinal juices from reaching the villi of the small intestine. In this embodiment, the second set of porosity regions 408 includes a helical wrapped film with an underlying sleeve. The helical wrapped film 408 may have a constant pitch angle or variable pitch angle. The variable pitch angle is depicted in FIG. 4B. Preferably, the pitch angle ranges from about 1 to 45 degrees and more preferably, it ranges from about 20 to 30 degrees. Obviously, the width of the helical film may also be adjusted to achieve similar results. Alternatively, the second set of porosity regions 408 could be applied as individual rings, rather than as a helical wrap. The helically wrapped film is preferably selected to have a minimum or no porosity, e.g., a FEP film.

Figure 5A:
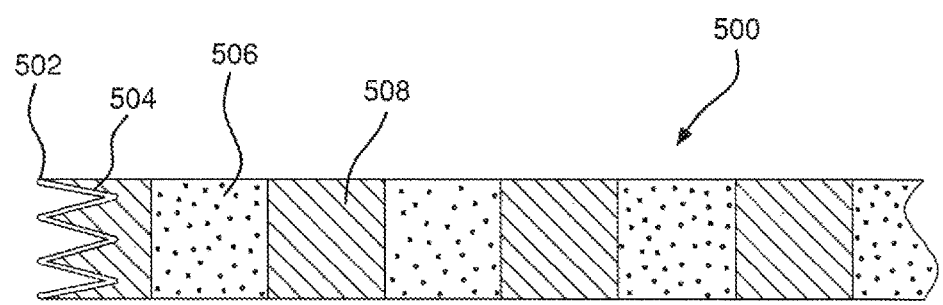
FIG. 5A illustrates an apparatus according to another embodiment of the invention.
Figure 5B:
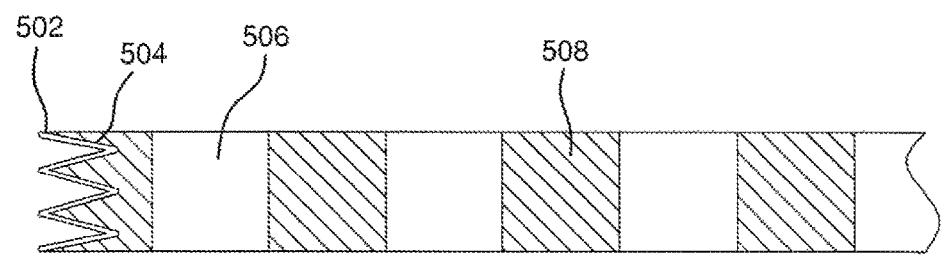
FIG. 5B illustrates an apparatus according to FIG. 5A after a predetermined time.

FIG. 5A illustrates an implantable apparatus according to another embodiment of the invention. FIG. 5B illustrates an implantable apparatus according to another embodiment of the invention.

Referring to FIG. 5A, an apparatus is generally depicted as reference number 500. The anchoring component 502 is attached to the sleeve with an adhesive 504. The adhesive 504 may be attached to any portion of the anchoring component 502 or as a fully covered portion of the anchoring component 502. For example, the adhesive 504 may be applied in a fillet pattern to a portion of the anchoring component 502. Preferably, the fillet pattern is utilized on both sides of the anchoring component 502. Again, the adhesive 504 may be arranged in any geometric pattern such as a circle, ring, line, and the like. The thickness and type of pattern utilized may be a factor in its strength. Alternatively, the anchoring component may be attached to the sleeve with a releasable component as described herein, e.g., as shown in FIGS. 1A-1C.

In this embodiment, the sleeve includes areas of different porosities. For example, the sleeve includes a plurality of first regions 506 and second regions 508 having different porosities. The first set of regions 506 permit nutrient absorption after a predetermined amount of time, e.g., it allows chyme and other gastrointestinal juices to reach the villi of the small intestine, allowing absorption of nutrients along that region. More specifically, the first set of porosity regions include a degradable cover material that degrades after a predetermined time. The degradable material may be a bioabsorable or biodigestible material as discussed herein. Preferably, the degradable material is a bioabsorable material such as PGA/PLA or other materials as known in the art. This coating may be applied to the entire sleeve or selected portions such as discrete rings or helical wrapped materials.

The second set of porosity regions 508 substantially minimizes or prevents nutrient absorption, e.g., it prevents or minimizes chyme and other gastrointestinal fluids from reaching the villi of the small intestine. In this embodiment, the second set of porosity regions 508 is a helical wrapped film over the underlying sleeve. The helical wrapped sleeve 508 may have a constant pitch angle or variable pitch angle. Preferably, the pitch angle ranges from about 1 to 45 degrees and more preferably, it ranges from about 20 to 30 degrees. Obviously, the width of the helical film may also be adjusted to achieve similar results. In this embodiment, as shown in FIGS. 5A and 5B, the second set of porosity regions 508 are applied as individual rings, rather than as a helical wrap. The helically wrapped film is preferably selected to have a minimum or no porosity, e.g., a FEP film.

Figure 6:
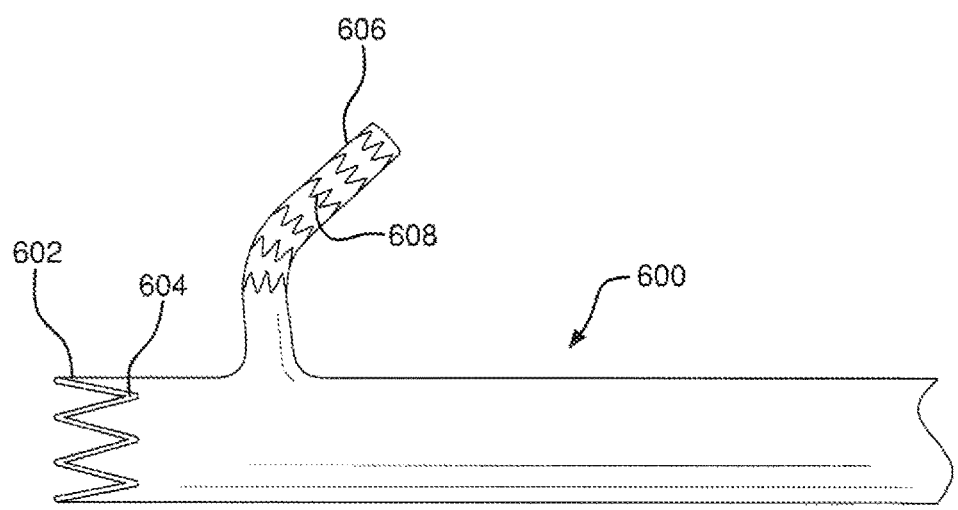
FIG. 6 illustrates an apparatus according to another embodiment of the invention.

FIG. 6 illustrates an implantable apparatus according to another embodiment of the invention.

Referring to FIG. 6, an implantable apparatus is generally depicted as reference number 600. The anchoring component 602 is attached to the sleeve with an adhesive 604 as described herein. Alternatively, the anchoring component may be attached to the sleeve with a releasable component as also described herein, e.g., as shown in FIGS. 1A-1C. The apparatus also includes a side branch portion 606 that may include another anchoring component 608. In this embodiment, the side portion 606 may be inserted into the common bile duct (not shown), thereby allowing bile duct drainage while excluding the chyme and other gastrointestinal fluids from the small intestine. The sleeve may be constructed to have regions of different porosities as described herein.

EXAMPLES

Without intending to limit the scope of the invention, the following examples illustrate how various embodiments of the invention may be made and/or used.

Example 1

In this example, a sleeve was fabricated and attached to an anchoring component with a releasable component, e.g., a bioabsorable material. A stainless steel mandrel and having an outer diameter of about 26 mm and a length of about 46 cm was obtained. An ePTFE sacrificial tube was pulled over the mandrel. The sacrificial tube had a wall thickness of about 0.01 mm, a length of about 40 cm, and an inner diameter of about 20 mm. This sacrificial tube was used in construction of the sleeve and would later be discarded.

Next, a substantially non-porous ePTFE film with a thermal adhesive layer FEP on one side was obtained. The composite film had a width of about 150 mm, a thickness of about 0.0025 mm, an isopropyl alcohol bubble point (IBP) of greater than about 0.6 MPa, and a tensile strength of about 309 MPa in the length direction (the strongest direction).

This first film was cut to be about 40 cm long. The first film with the thermal adhesive side up was longitudinally arranged on top of the sacrificial tube. The first film was arranged and cut to have about a 3 mm overlap, thereby creating a two-layer seam. The first film was applied so that its strongest direction was oriented in a direction that was substantially parallel to the longitudinal axis of the mandrel.

A second film including a substantially non-porous ePTFE film on one side and a thermal adhesive layer FEP on the opposite side was obtained. The second film had a width of about 25.4 mm, a thickness of about 0.0025 mm, an IBP of greater than about 0.6 MPa, and a tensile strength of about 309 MPa in the length direction (the strongest direction).

Two layers of the second film having the adhesive side down were then helically wrapped on top of the longitudinally wrapped film. The exposed film ends of the helically-wrapped film were heat-bonded (Weller Soldering Iron, Model EC2002 available from McMaster Carr, Santa Fe Springs, Calif.).

This fabricated assembly, i.e., the mandrel, sacrificial tube, and first and second film layers, were placed into a forced air oven (model NT-1000, Grieve Corporation, Round Lake, Ill.) set to about 320° C. for about 15 minutes in order to bond the first and second film layers together, thereby forming a sleeve on the sacrificial tube. The assembly was removed from the oven and allowed to cool to ambient temperature.

An anchoring component having about a 25.4 mm inner diameter self-expanding z-stent was constructed using nitinol wire having about a 0.51 mm diameter (part number SE508, Nitinol Devices and Components, Fremont, Calif.). The nitinol wire was wrapped onto an about 25.4 mm diameter stainless steel pin jig. The pin jig had about 1.52 mm diameter pins that were arranged to provide a single-ring, i.e., six-apex zig-zag pattern. The vertical distance between two adjacent apices from a center radius of the first apice to a center radius of an adjacent apice was about 19.1 mm. The ends of the wire were secured to the pin jig with screws. The jig was placed in a forced air oven (model HRF, Carbolite oven, Sheffield, England) set at about 450° C. for about 12 minutes. The jig was removed from the oven and quenched in water to cool it to an ambient temperature. The formed anchoring component was removed from the jig and the wire ends were trimmed as desired.

The anchoring component was placed over one end of the sleeve, which was still arranged on the sacrificial tube on the mandrel. The anchoring component portion was helically wrapped with one layer of an about 0.51 mm diameter copper wire to temporarily hold the anchoring component in place. Next, PLA/PGA resin at 85 weight percent PLA and 15 weight percent PGA (Durect® Corporation of Pelham, Ala.) was obtained and was dissolved in acetone (part no. 12271 from Ace Hardware of Oakbrook, Il). In this example, a sleeve was fabricated and attached to an anchoring component with a releasable component, e.g., bioabsorable material. A solution of about sixty weight percent acetone and about forty weight percent PLA/PGA (85/15) was applied to the anchoring component and the underlying sleeve material with a brush. The solution was allowed to air dry. The copper wire was removed and discarded and the sleeve attached to an anchoring component with a releasable component was removed from the mandrel. Finally, the sacrificial tube was removed from an internal surface of the finished device.

Example 2

In this example, a sleeve was fabricated to include a releasable component along a longitudinal a portion of the length of the sleeve. The releasable component enables disruption of the sleeve after a predetermined time, allowing for increased contact between the villi and chyme.

A stainless steel mandrel having an outer diameter of about 26 mm and a length of about a 46 cm long was obtained. An ePTFE sacrificial tube was pulled over the mandrel. The sacrificial tube had a wall thickness of about 0.01 mm, a length of about 40 cm, and an inner diameter of about 20 mm. This sacrificial tube was used in construction of the sleeve and would later be discarded.

Next, a substantially non-porous ePTFE film with a thermal adhesive layer FEP on one side was obtained. The composite film had a width of about 15.2 cm, a thickness of about 0.0025 mm, an IBP of greater than about 0.6 MPa, and a tensile strength of about 309 MPa in the length direction (the strongest direction).

The film was cut to be about 40 cm long. This film with the thermal adhesive side up was then longitudinally arranged on top of the sacrificial sleeve. The film was arranged and cut to have a 3 mm overlap, thereby creating a two-layer seam. The film was applied so that the strongest direction of the film was oriented in a direction that was substantially parallel to the longitudinal axis of the mandrel. Subsequently, the seam was heat-bonded with a soldering iron. (Weller Soldering Iron, Model EC2002 available from McMaster Carr, Santa Fe Springs, Calif.).

The fabricated assembly, i.e., the mandrel, sacrificial sleeve, and film, was placed in a forced air oven (model NT-1000, Grieve Corporation, Round Lake, Ill.) set to about 320° C. for about 15 minutes in order to bond the film together, thereby forming a sleeve on a sacrificial tube. The assembly was removed from the oven and allowed to cool to ambient temperature.

An anchoring component having about a 25.4 mm inner diameter self-expanding z-stent was constructed using nitinol wire having about a 0.51 mm diameter (part number SE508, Nitinol Devices and Components, Fremont, Calif.). The nitinol wire was arranged onto an about 25.4 mm diameter stainless steel pin jig. The pin jig had about 1.52 mm diameter pins that were arranged to provide a single-ring, i.e., six-apex zig-zag pattern. The vertical distance between two adjacent apices from a center radius of the first apice to a center radius of an adjacent apice was about 19.1 mm. The ends of the wire were secured to the pin jig with screws. The jig was placed in a forced air oven (model HRF, Carbolite oven, Sheffield, England) set at about 450° C. for about 12 minutes. The jig was removed from the oven and quenched in water to cool to ambient temperature. The formed anchoring component was removed from the jig and the wire ends were trimmed as desired.

The anchoring component was placed over one end of the sleeve, which was still arranged on the sacrificial tube on the mandrel. The anchoring component portion was covered with two wraps of the afore-mentioned film. The strength direction of the film was oriented perpendicular to the longitudinal axis of the mandrel and the adhesive side of the film faced down. The edges of the film were heated with a soldering iron (Weller Soldering Iron, Model EC2002 available from McMaster Carr, Santa Fe Springs, Calif.) to tack them in place.

A second sacrificial tube having a width of about 25.4 mm, thickness of about 0.013 mm, a methanol bubble point (MBP) of about 7 KPa, and a tensile strength of about 77 MPa in the length direction (the strongest direction) was arranged over the anchoring component and sleeve. Seven to ten layers of a sacrificial ePTFE film were then helically wrapped over the second sacrificial sleeve. The purpose of these seven layers of film and the second sacrificial sleeve was to impose a compression force on the underlying elements during a subsequent heating process, thereby bonding the non-porous ePTFE film to the stent.

The entire assembly was heated in a Grieve oven set to about 320° C. for about 15 minutes after which it was removed from the oven and allowed to air cool. The second sacrificial tube and seven to ten layers of a sacrificial ePTFE film helically wrapped over the sacrificial tube were removed and discarded. The remainder of the assembly was then removed from the mandrel and the first sacrificial sleeve was removed, thereby separating it from the anchoring component and sleeve. The ends of the sleeve were trimmed to have a total length of about 32.9 cm, that is, the anchoring component portion had a length of about 1.9 cm and the unanchored portion was about 31 cm in length.

The sleeve had a releasable component, e.g., a seam along the portion not attached to the anchoring component. The releasable component could be released, e.g., disrupted by applying internal pressure, such as through the use of a balloon catheter or similar device as known in the art.

This feature was tested with a release tool constructed from stainless steel tubing having a length of about 25.4 cm and an outer diameter of about 4.7 mm (Small Parts Inc, Miami Lakes, Fla.). In addition, silicone tubing (Jamak Corp, Weatherford, Tex.) having an outer diameter of about 6.35 mm and a length of about 7.62 cm was utilized in constructing the release tool.

The stainless steel tubing was closed at one end by inserting and adhering a water-tight plug machined from PVC barstock. The machined PVC barstock had a diameter that was similar to an inner diameter of the stainless steel tubing. A hole was drilled through one wall of the steel tubing at a location about 5.1 cm from the end with the water-tight plug. The drilled hole had a diameter of about 3.18 mm.

The silicone tube was arranged over the stainless steel tube and centered at the drilled hole. The silicone tube was tied down at each end with a glued linen thread. That is, a thread having a diameter of about 0.254 mm was attached to each end by wrapping the thread about thirty times around the silicone tube to attach the silicone tube to the stainless steel tube. Next, a cyanoacrylate glue was applied to the thread to further hold it in place. A luer fitting was then attached to the open end of the stainless steel tubing, thereby permitting a later connection to an inflation tool.

The release tool was inserted into the resultant sleeve of this example and inflated with an inflation tool (part number 622510, B. Braun, Bethlehem, Pa.), thereby applying a radial force to the sleeve. The pressure was increased at a rate of about 4 atm/min and the sleeve seam released, that is, it disrupted, at about 4 atm pressure.

Example 3

In this example, a sleeve was fabricated to have a porosity that changed after a predetermined time. More specifically, a sleeve was constructed to include porous and non-porous regions. The porous regions were coated with a bioabsorable material that degraded after a predetermined period of time.

A stainless steel mandrel had an outer diameter of about 26 mm and a length of about 46 cm was obtained. An ePTFE sacrificial tube was pulled over the mandrel. The sacrificial sleeve had a wall thickness of about 0.01 mm, a length of about 40 cm, and an inner diameter of about 20 mm. This sacrificial tube was used in construction of the sleeve and would later be discarded.

Next, a substantially porous ePTFE film with a thermal adhesive layer FEP on one side was obtained. The composite film had a width of about 15.2 cm, a thickness of about 0.01 mm, an MBP of about 7 KPa, and a tensile strength of about 77 MPa in the length direction (the strongest direction). Two layers of the film, with the thermal adhesive side up were longitudinally wrapped on top of the sacrificial sleeve with a 3 mm overlap thereby creating a four-layer seam. The film was applied so that the strongest direction of the film was oriented in a direction substantially parallel to the longitudinal axis of the mandrel.

Next, four layers of film having the same properties as the film above, except that they were about 1.3 cm wide, were helically arranged at about a 30° angle, up and back along the length of the longitudinally-applied film. The seam was heat bonded in place (Weller Soldering Iron, Model EC2002, McMaster Carr, Santa Fe Springs, Calif.). Black ink dots were applied to the film at about 2 cm intervals.

A substantially non-porous ePTFE film with a thermal adhesive layer of FEP on one side was obtained. This composite film had a width of about 2 cm, a thickness of about 0.0025 mm, an IBP of greater than about 0.6 MPa, and a tensile strength of about 309 MPa in the length direction (the strongest direction). One layer of this film was wrapped circumferentially around the previously-applied helically-wrapped film between every other ink mark and heat-bonded in place with the local heat source described above.

Next, the entire assembly was placed in a forced air oven (Grieve Oven, model NT-1000, Grieve Corporation, Round Lake, Ill.) set to about 320° C. for about 15 minutes. The assembly was removed from the oven and allowed to cool to ambient temperature. The assembly was then removed from the mandrel and the sacrificial tube was removed from the resultant film-tube. The resulting ePTFE film-tube possessed alternating porous and non-porous bands of equal width along the length of the tube. That is, regions of the film-tube were devoid of the non-porous film; such regions retained their porosity through the thickness of the wall.

A PLA/PGA resin at 85 weight percent PLA and 15 weight percent PGA (Durect® Corporation of Pelham, Ala.) was obtained and was dissolved in acetone (part no. 12271 from Ace Hardware of Oakbrook, Il). More specifically, a solution of about sixty weight percent acetone and about forty weight percent PLA/PGA resin (85/15) and was applied to the porous areas of the underlying ePTFE film tube using a brush. In this way, the pores of the film-tube sleeve were covered with a bioabsorable material.

Example 4

In this example, a sleeve was fabricated to include varied pore size along its length. A stainless steel mandrel having an outer diameter of about 26 mm and a length of about 46 cm was obtained. An ePTFE sacrificial tube was pulled over the mandrel. The sacrificial tube had a wall thickness of about 0.01 mm, a length of about 40 cm, and an inner diameter of about 20 mm. This sacrificial tube was used in construction of the sleeve and it would later be discarded.

A porous ePTFE film with a thermal adhesive layer (FEP) on one side was obtained. The composite film had a width of about 150 mm, a thickness of about 0.01 mm, an MBP of about 7 KPa, and a tensile strength of about 77 MPa in the length direction (the strongest direction).

Starting at one end of the mandrel two layers of the film with the adhesive side up were longitudinally arranged and trimmed on top of half of the length of the sacrificial tube to have a 3 mm overlap, thereby creating a four-layer seam. The film was applied so that the strongest direction of the film was arranged to be substantially parallel to the longitudinal axis of the mandrel.

A substantially non-porous ePTFE film with a thermal adhesive layer FEP on one side was obtained. The composite film had a width of about 150 mm, a thickness of about 0.0025 mm, an IBP of greater than about 0.6 MPa, and a tensile strength of about 309 MPa in the length direction (the strongest direction). One 20 cm long layer of film with the adhesive side up was longitudinally wrapped and trimmed around the other half the length of the sacrificial tube to have a 3 mm overlap creating a two-layer seam. This film was extended about 13 mm over the previously-applied film. The film was applied so that the strongest direction of the film was arranged to be substantially parallel to the longitudinal axis of the mandrel. The seams were heat-bonded (Weller Soldering Iron, Model EC2002, McMaster Carr, Santa Fe Springs, Calif.).

The entire assembly was then placed in a forced air oven (Grieve Oven, model NT-1000, Grieve Corporation, Round Lake, Ill.) set to a temperature of about 320° C. for about 15 minutes. The assembly was removed from the oven and allowed to cool to ambient temperature. The assembly was removed from the mandrel, and the sacrificial tube was removed from the resulting sleeve. The resulting sleeve comprised a porous section and a substantially non-porous section.

Test Methods:

This section describes measuring the tensile strength of the film. The tensile peak force was measured and averaged for ten samples using an Instron Model No. 5560 tensile testing machine (Canton, Mass.) equipped with Series 2714 Cord and Yarn grips. The jaw separation was 10.2 cm and the cross-head speed was 200 mm/min. The average of ten maximum load peak force measurements was used. The average of ten sample widths was calculated. Thickness was measured with Mitutoyo Snap Gage Model No. 547-400 (Nakatsugawa, Japan). The average of ten thickness measurements was used. Tensile strength was calculated as the quotient of tensile peak force and cross-sectional area of the tested samples.

Bubble point measurements were performed in accordance with the general teachings of ASTM E128-99. Isopropyl alcohol (Univar, Kirkland, Wash.) or methyl alcohol (Fisher Chemical, Fair Lawn, N.J.) was used as the test liquid. The tests were performed using about a 2.54 cm diameter test fixture. During the test pressure was increased at about 1.4 KPa/sec. The pressure corresponding to the appearance of the first stream of bubbles was identified as the bubble point. Tests performed using isopropyl alcohol yielded isopropyl alcohol bubble points (IBP) and tests performed with methyl alcohol yielded methyl alcohol bubble points (MBP). IBP measurements above 0.6 MPa could not be measured due to test equipment limitations. Bubble point values represent the average of 5 measurements.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. An implantable apparatus for placement in a gastrointestinal tract, said apparatus comprising:
    at least one anchoring component; and
    a sleeve having a length, a proximal end, and a distal end, wherein the sleeve includes a plurality of first porosity regions and a plurality of second porosity regions,
    wherein said first porosity regions permit nutrient absorption after a predetermined amount of time,
    wherein said second porosity regions prevent nutrient absorption,
    wherein said first porosity regions and said second porosity regions have an alternating configuration with respect to each other along said length of said sleeve, and
    wherein the at least one anchoring component is attached to the proximal end of the sleeve.

2. The apparatus of claim 1, wherein said first porosity regions and said second porosity regions are attached to each other by releasable components.

3. The apparatus of claim 1, wherein said sleeve is formed with a longitudinal seam along said length of said sleeve, said sleeve being attached together at said longitudinal seam with a releasable component.

4. The apparatus of claim 1, wherein said at least one anchoring component comprises a first anchoring component sized to be located in a patient's duodenum and a second anchoring component sized to be located in a patent's biliary duct.

5. The apparatus of claim 1, wherein said first porosity regions include a degradable cover material that degrades after a predetermined amount of time to permit said nutrient absorption.

6. The apparatus of claim 5, wherein the degradable cover material includes at least one of a bioabsorbable material and a biodigestible material.

7. The apparatus of claim 1, wherein the first porosity regions are attached to the second porosity regions by a releasable component that comprises sutures.

8. The apparatus of claim 1, wherein said second porosity regions comprise a helical wrapped film with an underlying sleeve.

9. The apparatus of claim 1, wherein said second porosity regions comprise individual rings of a non-porous film.

10. The apparatus of claim 1, wherein said first porosity regions comprise a plurality of pores, said pores being filled with a bioabsorbable or biodigestible material that degrades after a predetermined amount of time to permit said nutrient absorption.

11. The apparatus of claim 1, wherein the at least one anchoring component is a self-expanding stent.

12. The apparatus of claim 1, wherein the at least one anchoring component is a balloon expandable stent.

13. The apparatus of claim 1, wherein the second porosity regions are formed of fluorinated ethylene propylene (FEP).

14. The apparatus of claim 1, wherein the sleeve comprises an expanded polytetrafluoroethylene.

15. The apparatus of claim 1, wherein said first porosity regions comprise a bioabsorbable or biodigestible material coated on said sleeve as discrete rings.

16. The apparatus of claim 1, wherein said first porosity regions are present on said sleeve as distinct rings.

17. The apparatus of claim 1, further comprising a side branch component including an anchoring component.

18. The apparatus of claim 1, wherein said first porosity regions and said second porosity regions each have a wall thickness that changes over time.

* * * * *